(12) United States Patent
Nilsson et al.

(10) Patent No.: US 6,465,187 B1
(45) Date of Patent: Oct. 15, 2002

(54) METHOD OF TREATMENT

(75) Inventors: Gunnar Nilsson, Vattholma; Zou Xiang, Uppsala, both of (SE)

(73) Assignee: Innoventus Project AB, Uppsala (SE)

(*) Notice: Subject to any disclaimer, the term of this patent is extended or adjusted under 35 U.S.C. 154(b) by 0 days.

(21) Appl. No.: 09/566,787

(22) Filed: May 8, 2000

(51) Int. Cl.⁷ .......................... C12Q 1/68; C07H 21/04
(52) U.S. Cl. ......................... 435/6; 435/7.1; 536/24.5
(58) Field of Search ....................... 514/44; 536/24.5; 435/4, 6, 7.1, 91.2

(56) References Cited

U.S. PATENT DOCUMENTS

| | | |
|---|---|---|
| 5,843,773 A | 12/1998 | Shin et al. |
| 6,001,992 A | 12/1999 | Ackermann et al. |

OTHER PUBLICATIONS

Patzel et al. Nature Biotech 1998 Jan;16:64–68.*
Roush W. Science 1997 May;276:1192–3.*
Ishizuka et al. J Immunol 1999 Feb;162:2087–94.*
Finotto et al. J Clin Invest 1997;99:1721–28.*
Shapiro et al. Manual of Medical Therapeutics, 1986.*
Kay. Allergy Proc 1994;15:147–50.*
Otsuka, H., J. Denburg, J. Dolovich, D. Hitch, P. Lapp, R.S. Rajan, J. Bienenstock, and D. Befus. 1985. Heterogeneity of metachromatic cells in human nose: Significance of mucosal mast cells. *J. Allergy Clin. Immunol.* 76:695–702.
Reed, J. 1994. Bcl–2 and the regulation of programmed cell death. *J. Cell Biol* 124:1–6.
Dragovich, T., C. M. Rudin, and C. B. Thompson. 1998. Signal transduction pathways that regulate cell survival and cell death. *Oncogene* 17:3207–13.
Yee, N. S., I. Paek and P. Besmer. 1994. Role of kit–ligand in proliferation and suppression of apoptosis in mast cells: Basis for radiosensitivity of white spotting and steel mutant mice. *J. Exp. Med.* 179:1777–1787.
Hueber, A., G. Raposo, M. Pierres and H. He. 1994. Thy–1 triggers mouse thymocyte apoptosis through a bcl–2–resistant mechanism. *J. Exp. Med.* 179:785–96.
N. Katoh, S. Kraft, J. H. M. Wessendorf, T. Bieber. The high–affinity IgE receptor (FcεRI) blocks apoptosis in normal human monocytes. *J. Clin. Invest.* 105:183–190 (2000).
Lin, E., A. Orlofsky, M. Berger and M. Prystowsky. 1993. Characterization of A1, a novel hemopoietic–specific early–response gene with sequence similarity to bcl–2[1]. *J. Immunol.* 151:1979–88.
Chuang, P. I., E. Yee, A. Karsan, R. K. Winn and J. M. Harlan. 1998. A1 is a constitutive and inducible Bcl–2 homologue in mature human neutrophils. *Biochem. Biophys. Res. Commun.* 249:361–5.
S.S. Choi, S.H. Park, U.–J. Kim, H.–S. Shin. Bfl–1, a Bcl–2–related gene, is the human homolog of the murine A1, and maps to Chromosome 15q24.3. *Mammalian Genome* 8, 781–782 (1997).
Choi S.S., Park I.C., Yun J.W., Sung Y.C., Hong S.I., Shin H.S. A novel Bcl–2 related gene, Bfl–1, is overexpressed in stomach cancer and preferentially expressed in bone marrow. *Oncogene* 1995 Nov. 2; 11(9):1693–8.
Hamasaki, Al, F. Sendo, K. Nakayama, N. Ishida, I. Negishi, K. Nakayama and S. Hatakeyama. 1998. Accelerated neutrophil apoptosis in mice lacking A1–a, a subtype of the bcl–2–related A1 gene. *J. Exp. Med.* 188:1985–92.

* cited by examiner

*Primary Examiner*—James Ketter
*Assistant Examiner*—Q. Janice Li
(74) *Attorney, Agent, or Firm*—Burns, Doane, Swecker & Mathis, LLP

(57) ABSTRACT

A method of treatment of mast cell mediated inflammatory disorders in mammals comprising regulating the longevity and activity of activated mast cells by inhibiting the expression and/or function of the anti-apoptotic A-1/bfl-1 gene or gene product. The invention also provides the development and use of a compound capable of inhibiting the expression and/or function of the anti-apoptotic A-1/bfl-1 gene or gene product for the manufacture of a medicament for treating mast cell mediated inflammation in human tissues by regulating the longevity and activity of activated mast cells.

2 Claims, 11 Drawing Sheets

METHOD OF TREATMENT

FIELD OF INVENTION

The present invention relates to a method of treatment of mast cell mediated inflammatory disorders in mammals.

BACKGROUND OF THE INVENTION

The occurrence of allergic diseases has increased during the last decades, especially in the western world. Most allergic diseases are caused by IgE-mediated (immunoglobulin E) hypersensitivity reactions. Upon activation, during an allergic reaction, IgE molecules bind, via a cell-binding constant domain to specific receptors (FcεRI) on mast cells.

Mast cells are generally considered to be long living cells, that are widely distributed throughout vascularized tissues and certain epithelia where they play a fundamental role in the pathogenesis of immediate hypersensitivity reactions. In inflammatory disorders, such as allergies and asthma increased numbers of mast cells in affected tissues have been documented with a positive correlation between mast cell number and the severity of the allergic response symptoms. (Otsuka, H., J. Denburg, J. Dolovich, D. Hitch, P. Lapp, R. S. Rajan, J. Bienenstock, and D. Befus. 1985. Heterogeneity of metachromatic cells in human nose: Significance of mucosal mast cells. *J. Allergy Clin. Immunol.* 76:695–702.)

Upon activation and FcεRI aggregation, mast cells release preformed mediators such as histamine, proteases, tryptase and heparin, and synthesize lipid mediators and cytokines causing the allergic response observed in sensitized individuals. Survival, growth and differentiation of mast cells are regulated by cytokines such as interleukin-3 (IL-3) and stem cell factor (SCF). Mast cells have the capacity to survive the activation induced degranulation process, and to subsequently regranulate, enabling them to be activated again. Multiple rounds of mast cell activation may underlie the mechanism regulating the reoccurring inflammatory attacks of allergic patients during a pollen season. The possibility of regulating the longevity of activated mast cells could thus provide a treatment for mast cell mediated inflammatory disorders, such as allergies and asthma. However, the molecular mechanisms enabling activated mast cells to survive have not been elucidated.

A well documented mechanism for regulating cell longevity and survival is through the up-regulation of pro-survival genes belonging to the bcl-2 protein family. This is a growing family of apoptosis-regulatory genes, which may either be death antagonists (bcl-2, bcl-XL, bcl-w, mcl-1 and Al) or death agonists (bax, bak, bcl-XS, bad, bid, bik and hrk) [Reed, J. 1994. Bcl-2 and the regulation of programmed cell death. *J. Cell Biol* 124:1–6)]. Although the precise mechanism by which bcl-2 family members influence apoptosis is unkown, several lines of evidence suggest that bcl-2 proteins function at a critical decision point immediate upstream of an irreversible commitment to cell death [Dragovich, T., C. M. Rudin, and C. B. Thompson. 1998 Signal dransduction pathways that regulate cell survival and cell death. *Oncogene* 17:3207–13.]. It has been demonstrated that nerve growth factor (NGF) markedly increases bcl-2 expression in mast cells. When overexpressed, bcl-2 prolongs survival of mast cells following IL-3 deprivation. SCF and IL-3 induce suppression of apoptosis in mast cells by different mechanisms since IL-3 can induce bcl-2 induction but SCF cannot [Yec, N. S., I. Peak and P. Besmer, 1994 role of the c-kit ligand in proliferation and suppression of apoptosis in mast cells. Basis for radiosensitivity of white spotting and steel mutants. *J. Exp. Med.* 179:1777–1787.]. Despite the wide-ranging ability of bcl-2 to promote cell survival, there are circumstances where bcl-2 is not found to be responsible for protecting the cells from apoptosis [Hueber, A., G. Raposo, M. Pierres and H. He. 1994. Thy-1 triggers mouse thymocyte apoptosis through a bcl-2-resistant mechanism. *J Exp Med* 179:785–96.]. Therefore, it is possible that other members of the bcl-2 family may provide protective effects in some specific biological processes. In monocytes IgE-receptor aggregation leads to up-regulation of bcl-$X_L$ and bcl-2 (N. Katoh, S. Kraft, J. H. M. Wessendorf, T. Bieber. The high-affinity IgE receptor (FcεRI) blocks apoptosis in normal human monocytes. *J. Clin. Invest.* 105: 183–190 (2000)).

Al was originally identified from mouse bone marrow culture induced with granulocyte macrophage colony stimulating factor (GM-CSF) and bears structural homology to bcl-2 [Lin, E., A. Orlofsky, M. Berger and M. Prystowsky. 1993. Characterization of Al, a novel hemopoietic-specific early-response gene with sequence similarity to bcl-2. *J Immunol* 151:1979–88.]. Al was described as an early-response gene, expressed in multiple tissues such as thymus, spleen and bone marrow, and also expressed in a number of hemotopoietic cell lineages under various stimulations. These cells include T and B lymphocytes, macrophages, neutrophils [Chuang, P. I., E. Yee, A. Karsan, R. K. Winn and J. M. Harlan. 1998 Al is a constitutive and inducible Bcl-2 homologue in mature human neutrophils. *Biochem. Biophys. Res. Commun,* 249:361–5.], and endothelial cells [Lin, 1993, supra]. Al or the human homologue bfl-1 [S. S. Choi, S. H. Park, U. -J. Kim, H. -S. Shin. Bfl-1, a Bcl-2-related gene, is the human homolog of the murine Al and maps to Chromosome 15q24.3. *Mammalian Genome* 8, 781–782 (1997); Choi S. S., Park I. C., Yun J. W., Sung Y. C., Hong S. I., Shin H. S. A novel Bcl-2 related gene, Bfl-1 is overexpressed in stomach cancer and preferentially expressed in bone marrow. *Oncogene* Nov. 2, 1995; 11(9) :1693–8] is the only bcl-2 family member that is inducible by inflammatory cytokines such as tumor necrosis factor-α and IL-1β suggesting a possible role in mast cell biology.

Available drugs for allergic diseases treat the symptoms of the disease which occurs as a consequence of released mediators from inflammatory cells. A treatment that more specifically would prevent the allergic response, with reduced side effects, compared to current drugs, would be desirable.

Accordingly an object of the present invention is to provide a method for treatment of mast cell mediated inflammation.

SUMMARY OF THE INVENTION

The object of the invention is obtained by a method as claimed in the claims. According to the invention a method of treatment of mast cell mediated inflammatory disorders in mammals is provided. The method comprises regulating the longevity and activity of activated mast cells by inhibiting the expression and/or function of the anti-apoptotic A-1/bfl-1 gene or gene product. In a preferred embodiment the inhibition of the expression and/or function of the A-1/bfl-1 gene or gene product is obtained by targeting inflamed tissue in the affected mammal with a drug that inhibits the function.

According to a further aspect of the invention there is provided use of a compound capable of inhibiting the expression and/or function of the anti-apoptotic A-1/bfl-1 gene or gene product for the manufacture of a medicament for treating mast cell mediated inflammatory disorders in mammals by regulating the longevity and activity of activated mast cells.

According to a further aspect of the invention, a biological or chemical assay for identifying compounds for treatment of mast cell mediated inflammatory disorders in mammals is provided. The assay comprises using the anti-apoptotic A-1/bfl-1 gene or gene product as a molecular target.

According to another aspect of the invention, a method for development of drugs for treatment of mast cell mediated inflammatory disorders in mammals is provided. The method comprises using the anti-apoptotic A-1/bfl-1 gene or gene product as a molecular target.

According to the invention it was surpringly found that by inhibiting the anti-apoptotic function of A-1/bfl-1 gene or gene product the activated mast cells undergo apoptosis, preventing re-granulation and re-activation. In that way the number of activated mast cells in the inflammatory tissue can be reduced and the allergic symptoms alleviated. The present invention provides a means to selectively target and eliminate mast cells that are actively involved in mediating the inflammatory response.

From U.S. Pat. No. 6,001,992 targeting pro-survival genes with antisense compounds is known. U.S. Pat. No. 5,843,773 discloses the sequences of bfl-1 and the relation to cancer. Mast cell mediated inflammations are not disclosed.

DETAILED DESCRIPTION OF THE INVENTION

To investigate the role of Al/bfl-1 expression and function for the longevity of activated mast cells, a number of experiments were performed using mouse and human mast cells.

MATERIALS AND METHODS

Mast cell cultures. Bone marrow-derived cultured mouse mast cells (BMCMC) were obtained by culturing mouse (C57BL/6 or Al$^{-/-}$ [Hamasaki, A., F. Sendo, K. Nakayama, N. Ishida, I. Negishi, K. Nakayama and S. Hatakeyama. 1998. Accelerated neutrophil apoptosis in mice lacking Al-a, a subtype of the bcl-2-related Al gene. *J Exp Med* 188:1985–92.], 4- to 5-week old,) bone marrow cells for 5 to 6 weeks in 10% WEHI-3 (IL-3 producing cell-line) enriched conditioned RPMI 1640 medium, supplemented with 10% heat-inactivated fetal bovine serum (Gibco-BRL, Germany), 4 mM L-glutamine, 50 μM 2-mercaptoethanol (Sigma Chemical Co., St. Louis, Mo.), 1 mM sodium pyruvate (Sigma), 0.1 mM non-essential amino acids (Sigma), 10 mM Hepes (Sigma), and 100 μg/ml penicillin/streptomycin. The mast cell differentiation was confirmed by toluidine blue staining. The growth factor dependent mouse mast cell line MCP5/L was maintained in the same medium described above. For cell viability assays, the cell suspension was mixed with the vital dye, trypan blue, and only the number of live cells was scored.

Cord blood cultured human mast cells (CBCMC) were differentiated from cord blood cells cultured for 8–10 weeks in 50 ng/ml SCF and 10 ng/ml IL-6 (Pepro Tech, London UK) and complete RPMI medium. The purity of human mast cells was >95% by tryptase staining.

Activation of mast cells in vitro. For FcεRI-dependent activation, MCP5/L cells were resuspended at 1×10$^6$ cells/ml and sensitized using a monoclonal murine IgE anti-TNP (trinitrophenyl) (IgEl-b4, ATCC, Manassas, Va.) antibody (15% hybridoma supernatant) for 90 min. The cells were washed twice with warm medium, followed by challenge with 1 μg/ml TNP-BSA for time periods indicated. For cell viability assays, both the anitbody sensitization and the anitgen challenge were performed in RPMI medium supplemented with 0.5% BSA (Sigma) at 37° C. in a humidified incubator containing 5% CO2. For gene regulation studies, all the incubations were carried out in RPMI medium supplemented with 5% fetal bovine serum and antibiotics on a rocker platform. In some experiments, cells were cross-linked in the medium containing 1 mM EDTA or cells were incubated in ice-cold water during FcεRI cross-linking. Where indicated, various inhibitors were introduced to test their effects on A1 regulation after FcεRI cross-linking. These include bisindolylmaleimid (100 nM), wortmannin (100 nM), SB 203580 (pyridinylimidazole compound, inhibitor of p 38 mitogen-activated protein kinase) (1 μM), PD 98059 (2-(2-amino-3-methoxyphenyl)-4-oxo-4H-[1] benzopyran, inhibitor of mitogen-activated protein kinase Kinase-1 (MEK1)) (10 μM), genistein (1 μM), suramin (100 μM), cyclosporin A (2 μg/ml), dexamethasone (1 μM) and cycloheximide (10 μg/ml). Dexamethasone and suramin were added 14 hr and 24 hr, respectively, before IgE sensitization. All the other inhibitors were added at the same time as FcεRI aggregation. In some A1 regulation assays, cells were resuspended in medium containing calcium ionophores (ionomycin) and compound 48/80 (N-methyl-p-methoxyphenethylamine) as well as cytokines including IL-3, IL-4, SCF, GM-CSF (granulocyte-macrophage colony stimulating factor) and TNF-α (tumour necrosis factor) and incubated for 6 hr at 37° C. on a rocker platform. After various treatments mentioned above, cell pellets were collected and kept at −80° C.

Human myeloma IgE (ND) and mouse anti-human IgE (clone 346) were used to activate CBCMC through cross-linkage of the high-affinity IgE-receptor. Human mast cells at 1×10$^6$ cells/ml were incubated with 1 μg/ml IgE overnight, washed twice with PBS, plated at 3×10$^5$ cells/ml, and challenged with 2.0 μg/ml anti-IgE for 30 min at 37° C.

Cell viability measurement. Trypan blue exclusion assay was used in all of the cell survival experiments. In brief, cell suspension was mixed with the vital dye, trypan blue, and the number of live cells was scored. In some cases, cell apoptosis was also measured by Cell Death Detection ELISA (Boehringer Mannheim, Mannheim, Germany) quantitatively detecting the mono- and oligonucleosomes released into culture supernatant.

Isolation of RNA and RNAse Protection Assay (RPA) analysis. Total cellular RNA was isolated using the TriPure isolation reagent (Boehringer Mannheim, Mannheim, Germany). RPA was performed using the mAPO-2 and hAPO-2 multi-probe set from the RiboQuant System (PharMingen, San Diego, Calif.) following the supplier's recommended protocol. Briefly, 10 μg of RNA was hybridized overnight at 56° C. with the $^{32}$P-labelled probes synthesized from the mAPO-2/h-APO-2 multi-probe template set. Protected fragments were precipitated and size fractionated by 5% polyacrylamide gels. Pixel intensity was determined using a phoshoimaging device. Levels of each gene transcript were quantified by MacBas V2.2 (Fuji Photo Film Co. Ltd., Japan).

Measurement of release. For detection of the granule-associated N-acetyl-β-D-hexosaminidase (β-hexosaminidase), an enzymatic colorimetric assay was used. Supernatant or a combination of supernatant and cell lysate was mixed with identical volume of substrate solution (7.5 mM p-nitrophenyl N-acetyl-β-D-glucosaminide (Sigma) in 80 mM citric acid, pH 4.5), and incubated at 37° C. for 2 hr. The reaction was stopped by adding glycine (0.2 M, pH 10.7) into each well and the absorbance was measured. Percentage of β-hexosaminidase release is calculated as the absorbance of the supernatant over that of the combination of supernatant and lysate.

Statistical Analysis

Statistics were calculated using an analysis of variance (ANOVA), followed by multiple comparison using Fisher's method. * denotes $p<0.05$, ** $p<0.01$. Values presented are the means±SEM.

Figure Legends

FIG. 1. Survival promotion of mast cells after cross-linkage of FcεRI (IgE CL). MCP5/L cells (A) or BMCMC from C57BL/6 (B and C) were either stimulated through cross-linkage of FcεRI or left untreated in RPMI medium deprived of serum and growth factors. Cell viability was determined by trypan blue exclusion and presented as the percentage of input cells that are still surviving when examined every 24 hours (A and B). In C, cell apoptosis was assessed by ELISA measuring the release of nucleosomes into the culture supernatant after 24 hours.

FIG. 3. Bcl-2 family gene regulation in mouse mast cells after cross-linkage of FcεRI (IgE CL), (A) RPA was performed to analyze the expression levels of the indicated genes on total RNA isolated from MCP5/L cells either unstimulated or activated for 6 hours through FcεRI cross-linkage. Lane 1, untreated, normal cultured cells. Lane 2, control cells that were incubated and washed through the same procedures needed for FcεRI cross-linkage. Lane 3, cells that were stimulated through FcεRI cross-linkage. (B) Phosphoimaging signals presented in A (lanes 2 and 3) are shown as gene expression relative to the average expression of the house keeping genes GAPDH and L32. Data were normalized such that the densitometric level of each gene from the control cells was given a value of 1.

FIG. 4. Bcl-2 family gene regulation in human mast cells after cross-linkage of FcεRI (IgE CL). RPA was performed to analyze the expression levels of the indicated genes on total RNA isolated from CBCMC either unstimulated or activated through FcεRI cross-linkage for 2, 6, and 12 hr (A) and phosphoimaging signals of the A1 gene (B) are densitometrically measured as explained in FIG. 3.

FIG. 5. Time-dependent up regulation of A1 gene. RNA was isolated from MCP5/L cells activated through FcεRI crosslinkage for various time points as indicated and RPA was performed to analyze the kinetics of A1 induction.

FIG. 6. Regranulation of mouse mast cells. MCP5/L cells were activated through FcεRI cross-linkage up to 24 hours, the cells were then washed and incubated under normal culture condition. 48 hours after the first activation, cellular IgE receptors were cross-linked again. A1 induction at time points both in the first (1st CL) and the second (2nd CL) activation periods (A) and β-hexosaminidase (β-hex) release 30 min after cross-linkage (B) were assayed as explained in FIG. 8.

FIG. 7. The effects of ionomycin (A) and compound 48/80 (B) on A1 induction, release and survival of MCP5/L cells. RPA was performed on RNA derived from cells incubated for 6 hours in the presence of ionomycin or compound 48/80 at concentrations indicated (upper panels). Release of β-hexosaminidase (β-hex) after 30 min is shown (middle panels) as explained in FIG. 8. Survival rate of mast cells after 4 days in medium deprived of serum and growth factors was measured (lower panels) as explained in FIGS. 1, A and B.

FIG. 8. Effects of cold incubation and EDTA treatment on A1 induction and mast cell degranulation. (A) RPA was performed on RNA derived from MCP5/L cells activated through FcεRI crosslinkage for 6 hr, with or without the presence of EDTA (1 mM), and where indicated, cells were also crosslinked in cold (ice-water). (B) and (C) levels of β-hexosaminidase (β-hex) in the supernatants from either control cells or cells stimulated through IgE-receptor cross-linkage for 30 min, in the absence or presence of various concentrations of EDTA (B), or in cold incubation (C), were determined as a measurement of activation and de-granulation by an enzymatic colorimetric assay FIGS. 9a–9b Effects of inhibitors on induction of A1. RPA was performed on RNA derived from MCP5/L cells stimulated for 6 hr through FcεRI crosslinkage in the presence of various inhibitors as indicated. Densitometric analyses are shown as the A1/L32 ratio. A1 induction for activated cells without inhibitors was taken as 100.

FIG. 11. Absence of survival promotion of mast cells from $A1^{-/-}$ mice after FcεRI cross-linkage (IgE CL). (A) β-hexosaminidas (β-hex) release from A1−/− mast cells was assessed as explained in FIG. 6 to show that the cells were activated and released β-hexosaminidase. (B) BMCMC from A1 knock-outs were stimulated and viability was determined as explained in FIG. 1B.

Results

Figure 1A:
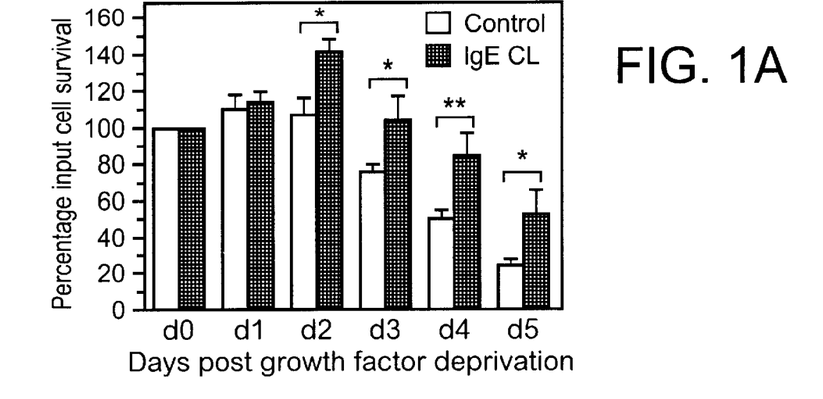
Figure 1B:
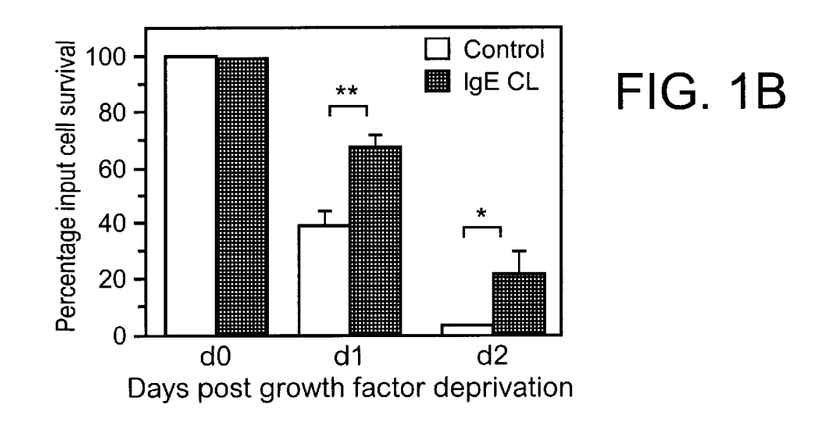

IL-3 is one of the primary growth factors for mast cells. MCP5/L is a growth factor-dependent mouse mast cell line, which requires the inclusion of IL-3 in its medium for survival and proliferation. First it was determined whether mast cells undergo apoptosis upon withdrawal of WEHI conditioned medium, (which forms the source of IL-3). As shown in FIG. 1A, withdrawal of WEHI from MCP5/L mast cells, resulted in a progressive decrease in the number of live cells as determined by trypan blue exclusion staining. To examine whether mast cell activation would influence this apoptotic process following withdrawal of growth factor, MCP5/L cells were activated through FcεRI aggregation. As also shown in FIG. 1, percentage cell survival of activated cells, demonstrated by trypan blue exclusion, increased as compared with control cells after 2 days of incubation.

On day 4 and 5, FcεRI aggregation caused cell survival to increase about 70% and 120%, respectively, over control cells.

Figure 1C:
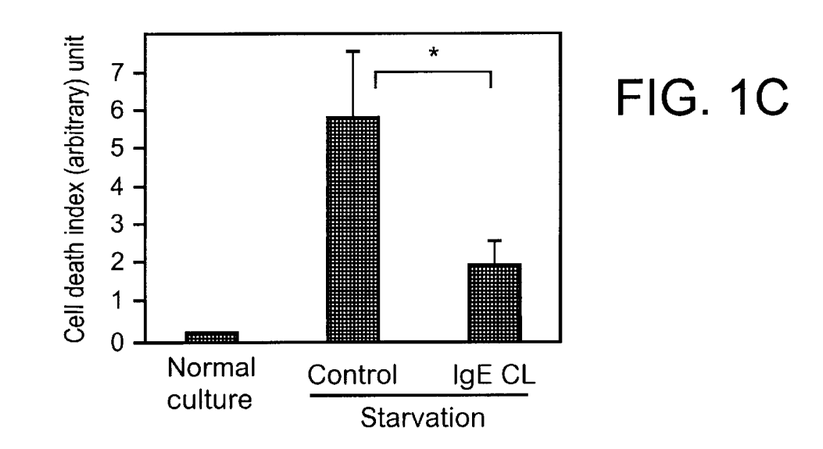
Figure 2:
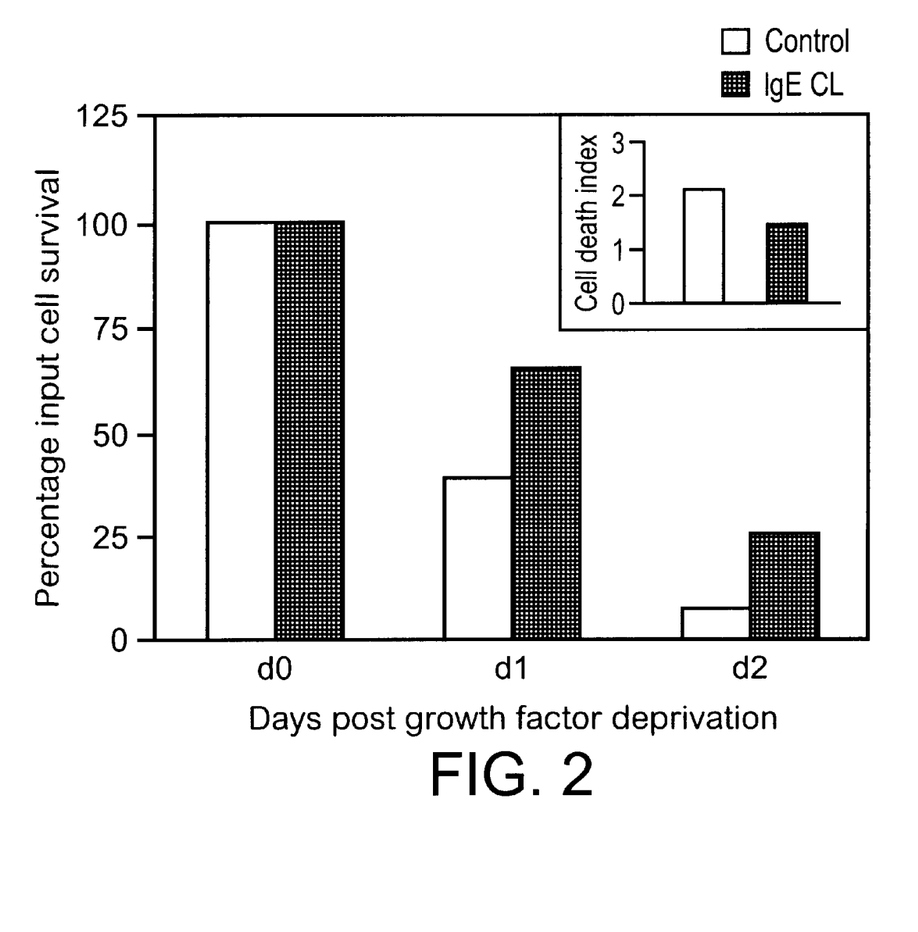
FIG. 2. Survival promotion of human mast cells after cross-linkage of FcεRI (IgE CL). Survival of human CBCMC was assessed as explained in FIG. 1. Inset indicates levels of nucleosome release shown in arbitrary units.

Similar findings were obtained using mouse BMCMC (FIG. 1B) and human CBCMC (FIG. 2) although withdrawal of exogenous growth factors resulted in a more rapid decrease in viability as compared with the mouse cell line. Two days following the IgE crosslinkage, survival rate of the activated cells surpassed that of the control cells by 400% and 250%, respectively, for BMCMC (FIG. 1B) and CBCMC (FIG. 2). By measuring release of mono- and oligo-nucleosomes we could confirm that cross-linkage of FcεRI rescued the cells from undergoing apoptosis (FIG. 1C and FIG. 2, inset). Thus, activation of mast cells through the high-affinity IgE-receptor initiates a cellular response that directly prevents apoptosis, without addition of growth factors.

Figure 3A:
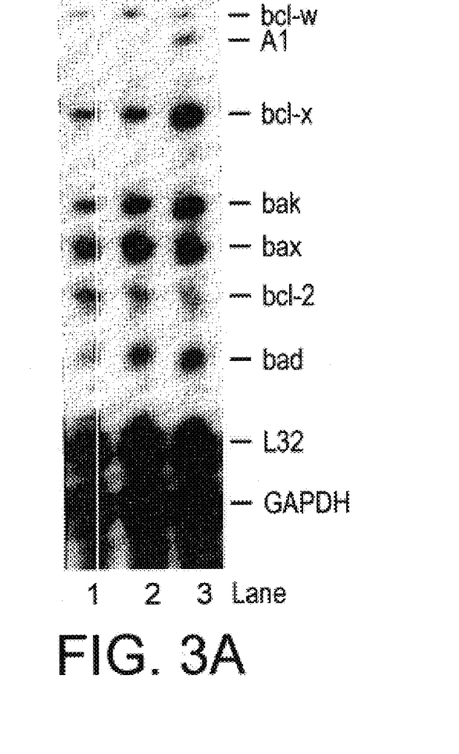
Figure 3B:
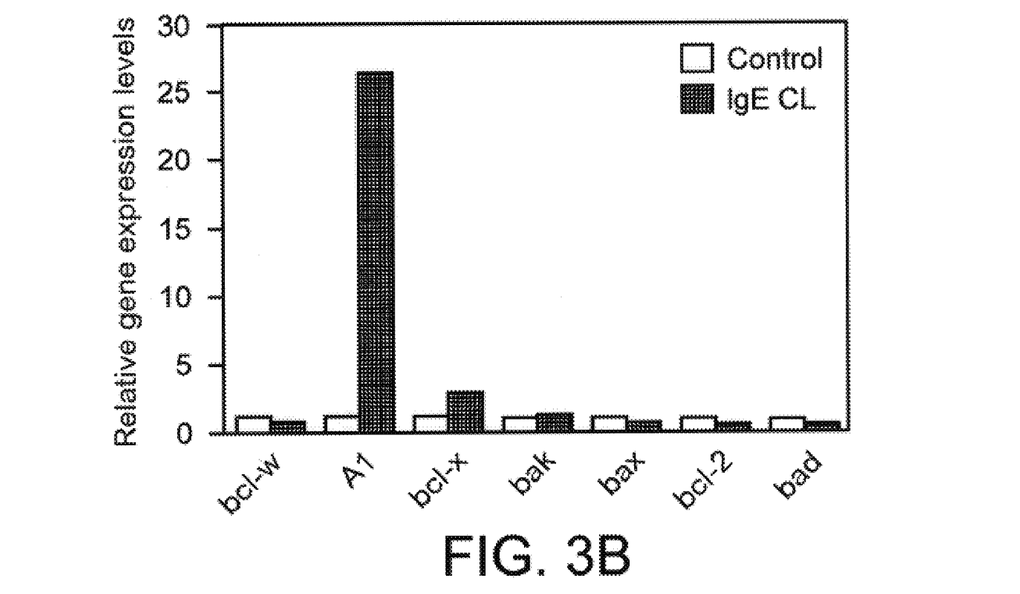

To determine whether mast cells transcribe any of the apoptosis-related genes constitutively or following activation (FcεRI aggregation), RPA and densitometric analysis were performed. By using the mAPO-2 multi-probe set from PharMingen, the expression pattern of murine bcl-2 family genes were analyzed (FIG. 3). A striking up-regulation of the pro-survival bcl-2 homologue A1 was observed, following FcεRI aggregation for 6 hr. Serum starvation and growth factor withdrawal could not induce A1 expression (FIG. 3A). For other genes analyzed, no obvious regulation was seen directly from the desitometric analyses. The expression of A1 in mast cells was confirmed using C57, another murine mast cell line and BMCMC (data not shown).

Similarly, hAPO-2 multi-probe set was used to analyse the human bcl-2 family gene regulation. A strong induction of the human homologue of murine A1, bfl-1 was found, following 2 hr of FcεRI activation (FIG. 4A) and the quantitative densitometric analyses showed an up-regulation of the gene by over 100 fold as compared with control cells (FIG. 4B).

Figure 5:
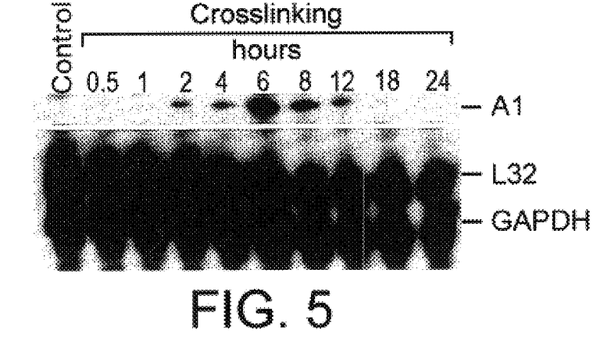

RPA was also performed to determine the kinetics of A1 expression. Cells were sensitized with monoclonal IgE for 90 min before FcεRI aggregation with TNP-BSA. Cells were harvested at the time points indicated (FIG. 5). Following FcεRI aggregation, A1 RNA was first detected at 2 hr, peaked around 6 hr, and was no longer detectable by 24 hr.

Figure 4A:
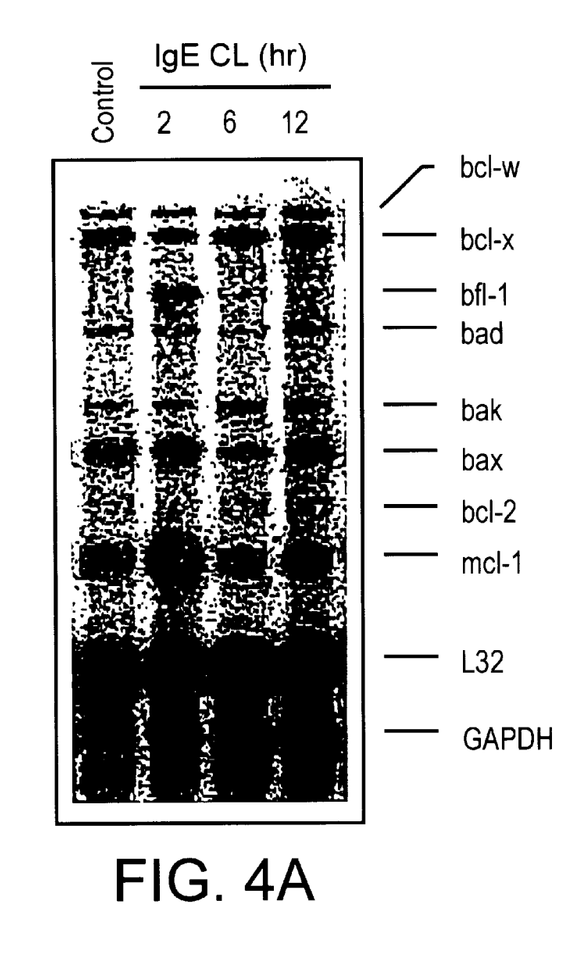
Figure 4B:
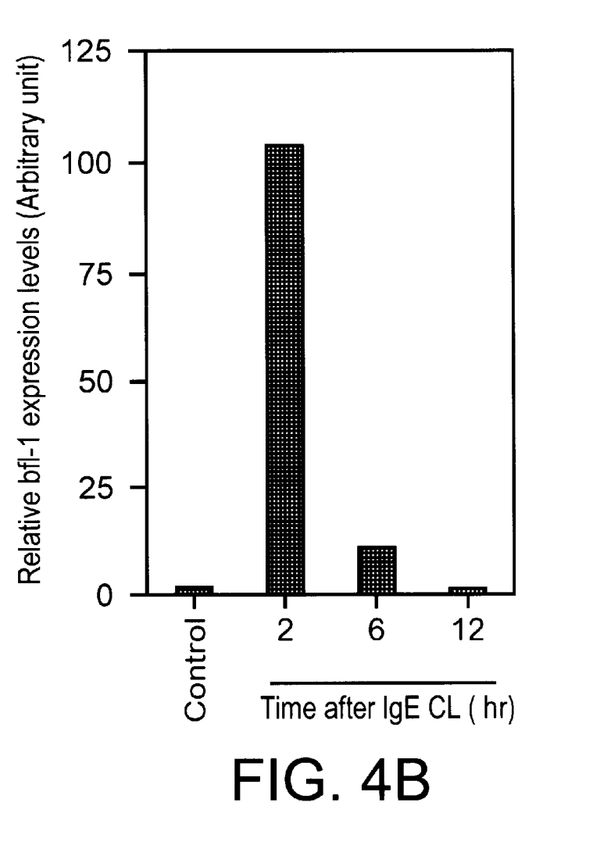

In contrast to mouse cells, bfl-1 in CBCMC was both induced and declined more rapidly (FIG. 4A).

Figure 6A:
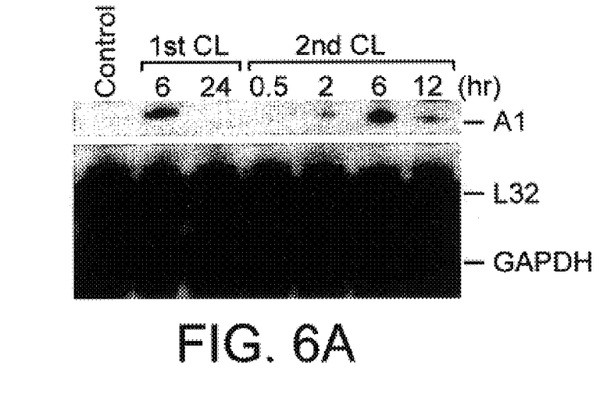
Figure 6B:
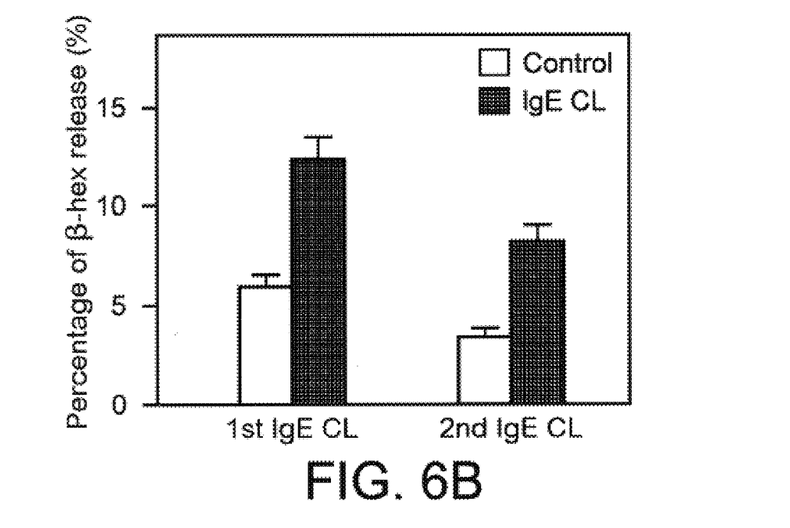

As seen in FIG. 5, A1 expression following FcεRI aggregation peaked by 6 hr and disappeared after 18 to 24 hr. Under physiological conditions, mast cells do not die after degranulation triggered by FcεRI aggregation and they can be activated again. Therefore it was tested whether, after the first activation, A1 could be induced again by a second FcεRI aggregation. 24 hr after the first activation, cells were washed, maintained in complete culture medium for another 24 hr, and then activated again by FcεRI FcεRI aggregation. Similar with the kinetics of a single activation (FIG. 5), A1 appeared 2 hr after the second FcεRI aggregation, and peaked around 6 hr (FIG. 6).

Figure 7A:
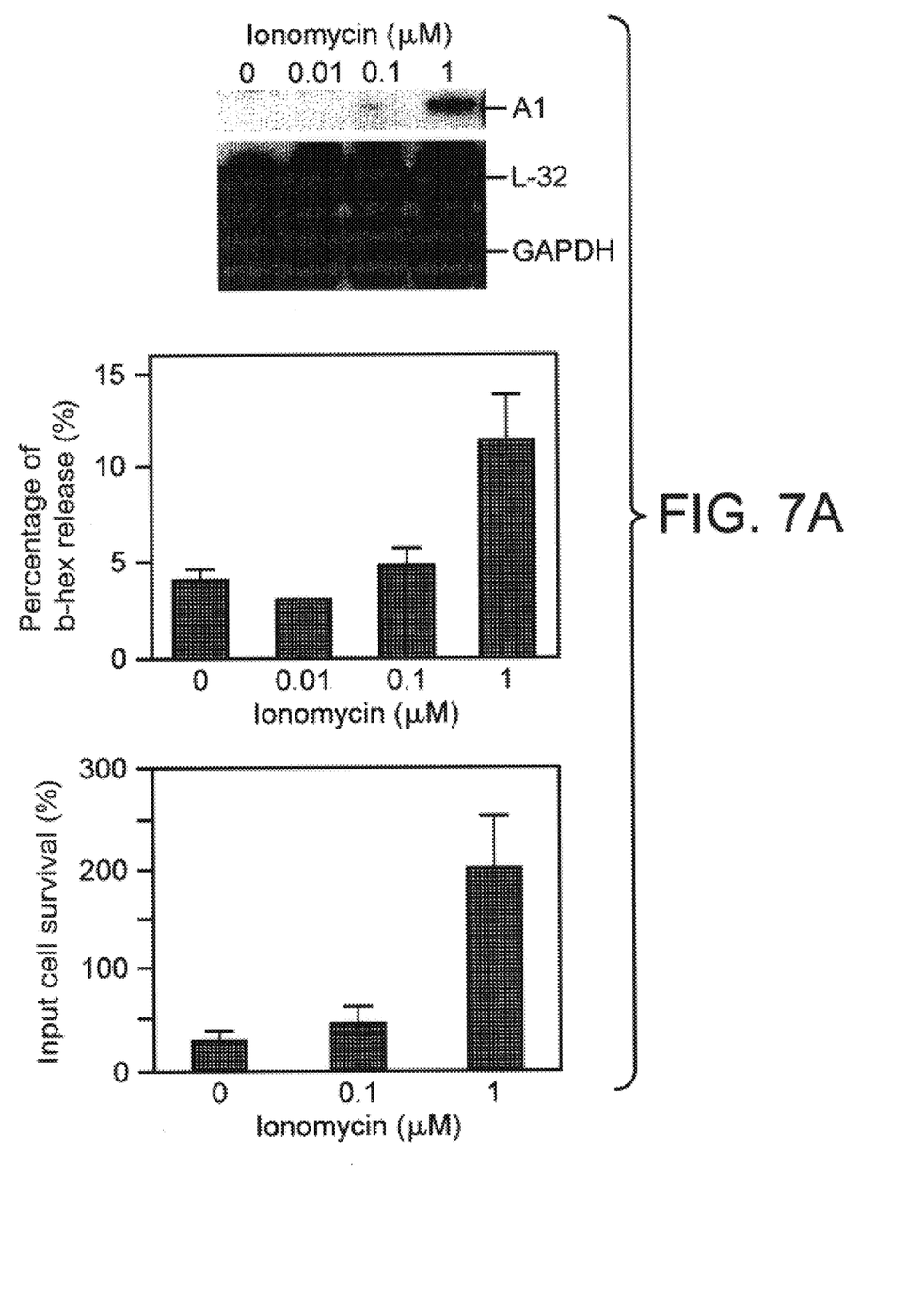
Figure 7B:
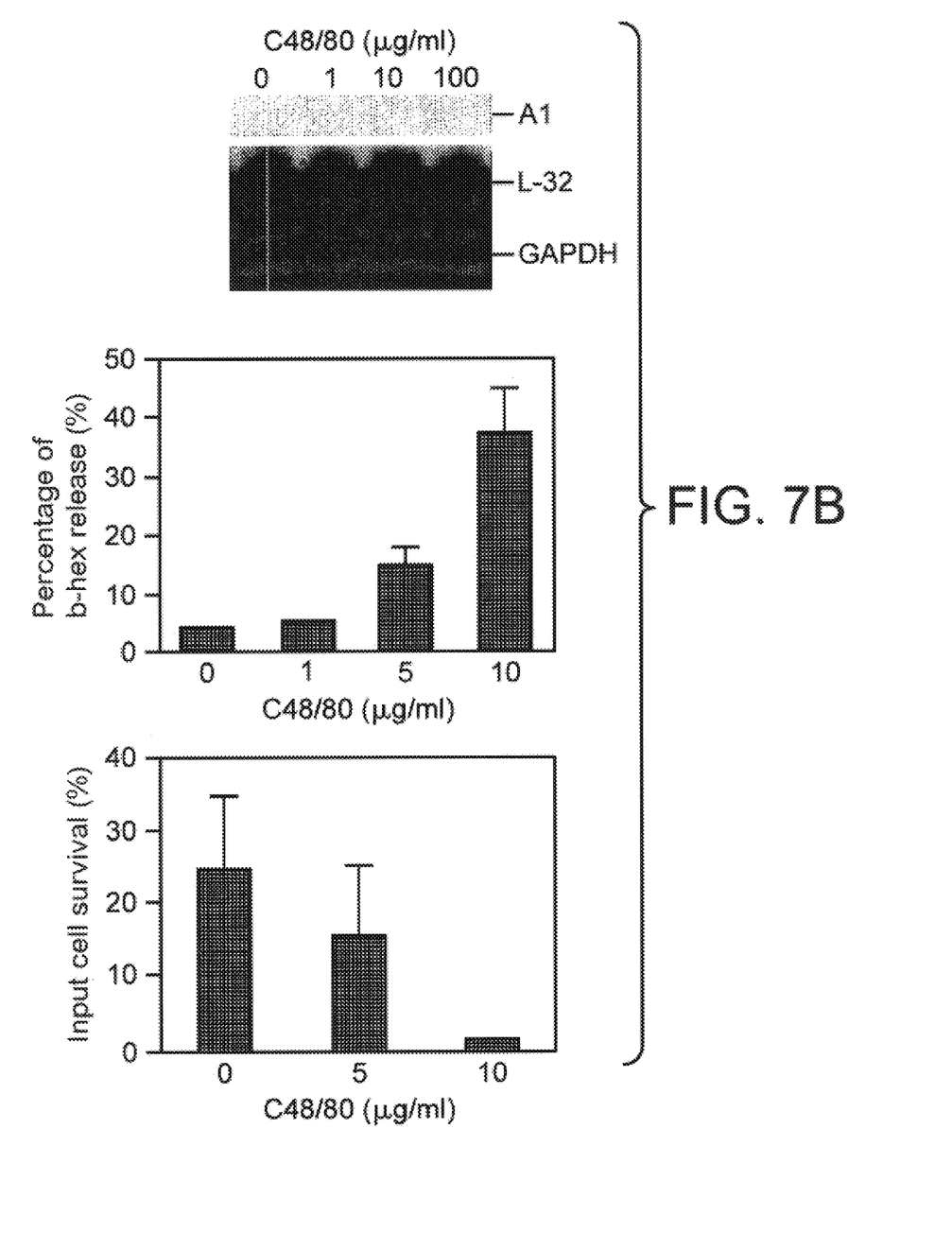

To determine whether the regulation of A1 transcript was only seen with FcεRI aggregation as a physiologic stimulus, mast cells were also exposed to ionomycin and c48/80 for 6 hr. As shown in FIG. 7A, ionomycin also induced expression of A1 and promoted mast cell survival. In contrast, c48/80 at concentrations of up to 1 mg/ml had no effect on A1 gene transcription (FIG. 7B). Under the concentrations used, c48/80 triggered substantial β-hexosaminidase release but the cells did not survive.

Figure 8A:
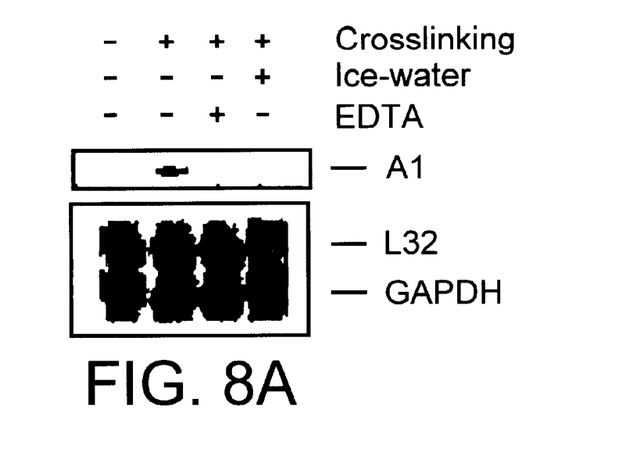
Figure 8B:
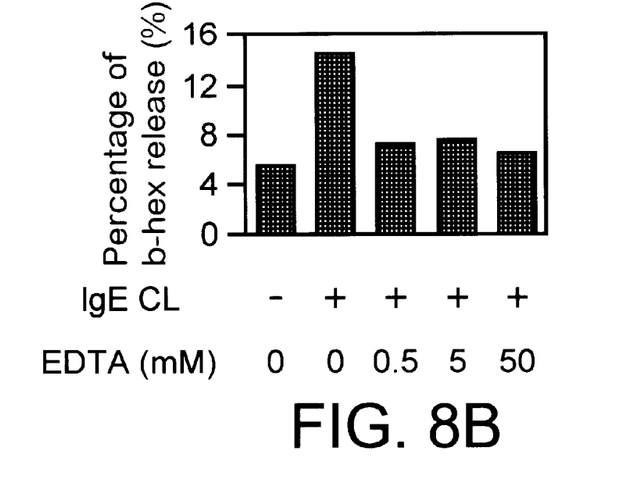
Figure 8C:
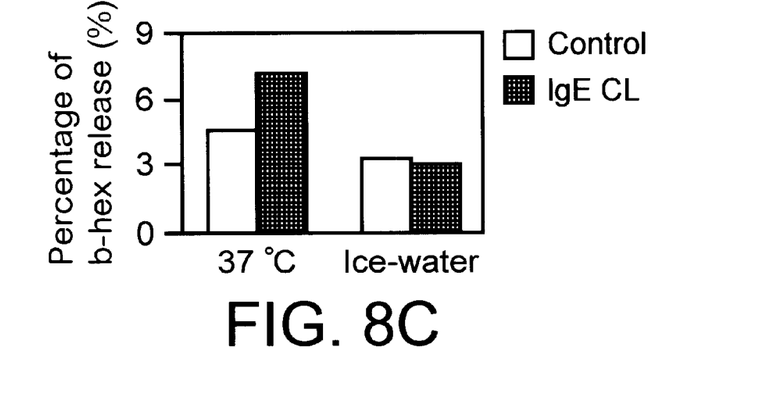

In efforts to gain insight as to whether A1 expression is mediated by calcium influx following mast cell activation it was determined whether A1 was up-regulated upon FcεRI aggregation in the presence of EDTA or when the cells were incubated in ice-cold water. Remarkably, both EDTA and ice-cold water treatments blocked A1 expression induced by FcεRI aggregation (FIG. 8A). EDTA can block the calcium mobilization of mast cells and thereby inhibit release of mast cell granular enzyme β-hexosaminidase following FcεRI aggregation (FIG. 8B). Similarly, when incubated in ice-cold water, β-hexosaminidase release was also inhibited (FIG. 8C).

Figure 9A:
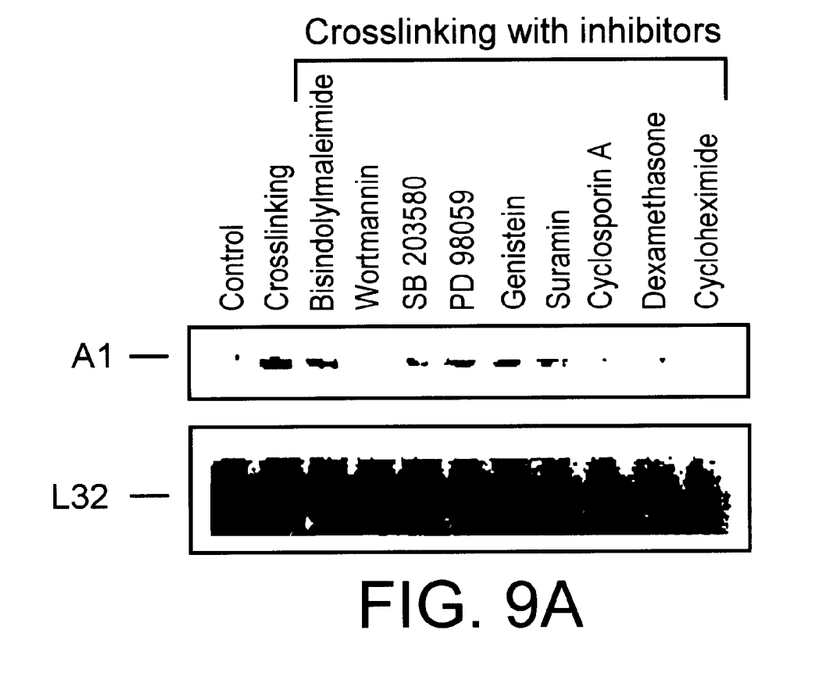
Figure 9B:
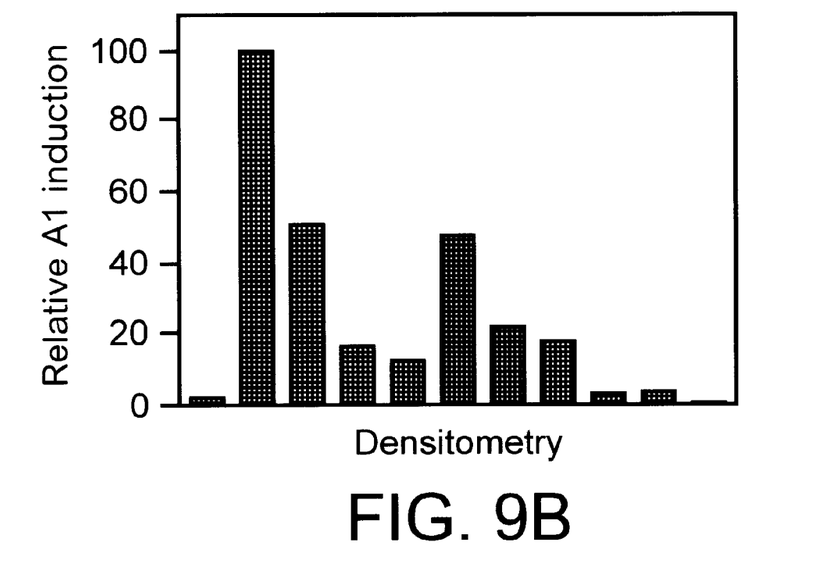

The effects on A1 induction of a number of inhibitors that are directed against various signal transduction pathways were also tested and densitometric analysis was performed (FIG. 9). Wortmannin, a PI-3 kinase inhibitor, cyclosporin A, an immunosuppressive agent, and cycloheximide, an inhibitor of de novo synthesis of early gene products, and dexamethasone, a glucocorticoid, could completely block A1 induction.

Figure 10:
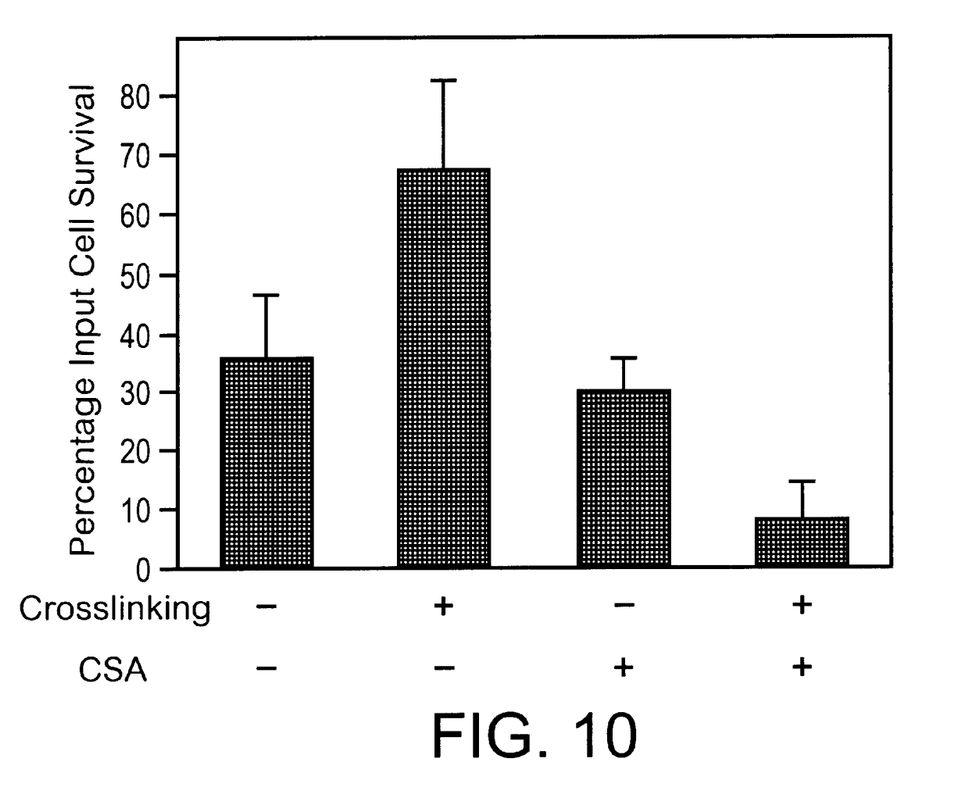
FIG. 10. Effect of cyclosporin A (CSA) on the survival promotion of mast cells through FcεRI crosslinkage. MCP5/L cells were either stimulated through FcεRI or left untreated for 5 days in medium deprived of serum and growth factors. For some experiments CSA was added at a contraction of 2 µg/ml. Viability was determined by trypan blue exclusion.

It was further tested whether CSA could block the survival promotion of mast cells triggered by FcεRI crosslinkage. CSA did not affect control MCP5/L apoptosis, However, when cells were activated through IgE receptor crosslinkage, addition of CSA dramatically reduced the number of live cells (FIG. 10). Similar results were obtained by wortmannin and dexamethasone (data not shown).

Figure 11A:
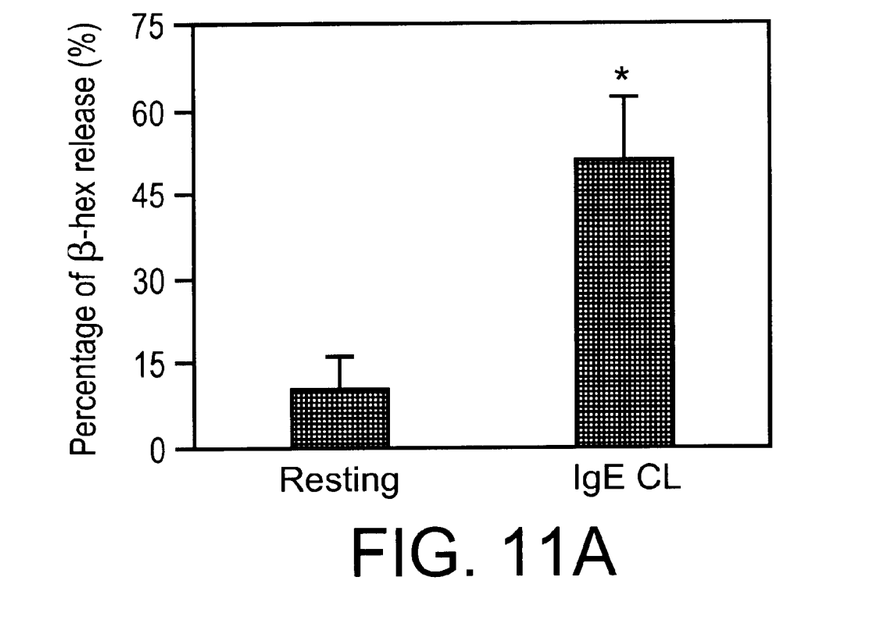
Figure 11B:
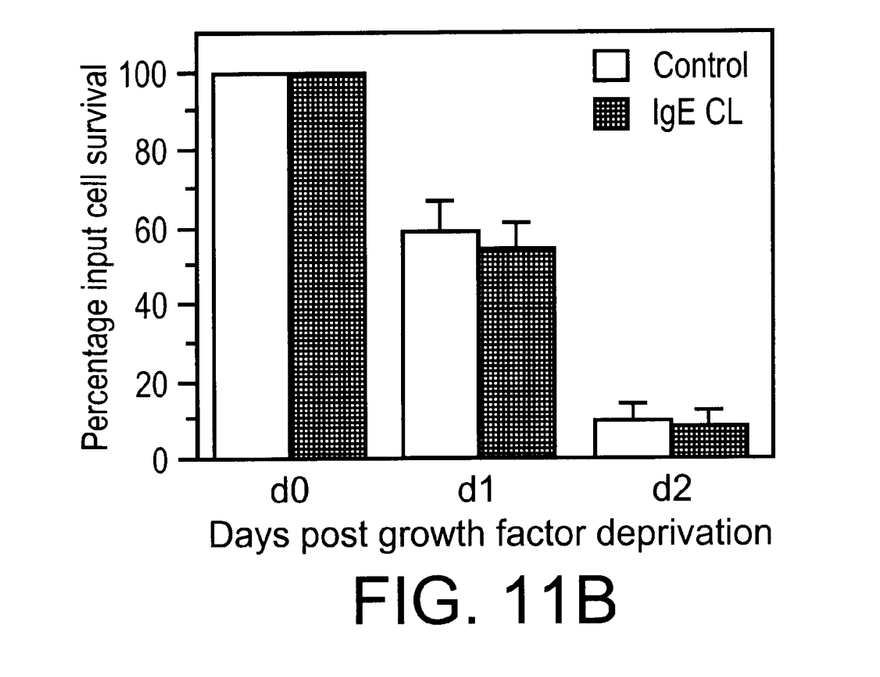

To address the issue whether A1 is a prerequisite for mast cell survival upon cross-linkage of FcεRI, or if the up-regulation of A1 is just a parallel phenomenon, mast cells deficient in A1 were used. Upon activation with IgE and antigen the A1$^{-/-}$ BMCMC released granule associated β-hexosaminidase similar to wild-type control (FIG. 11A). Cross-linkage of FcεRI did not promote survival of these cells, but they died at the same rate as resting control cells (FIG. 11B). This finding confirms the hypothesis that A1 expression is necessary for mast cell survival upon allergic activation.

In the present invention the pro-survival gene A1/bfl-1 has been identified to be crucial for mast cell survival after activation of mast cells through the high affinity IgE receptor. Interfering with the transcriptional regulation, the expression of A1/bfl-1, the activity of the A1/bfl1 protein, or its interaction with pro-survival genes can be used to prevent mast cells to survive an alergy-associated activation. The present invention provides a method to develop drugs and to treat various disease in mammals where a local activation of mast cells are of importance for the symptoms. Thus it can be used to treat e.g. nasal mucosa in hay fever, respiratory tract in asthma, the skin in atopic dermatitis, the gastrointestinal tract in food allergy etc. The resulting drug of the invention which could be a protein, a (poly)peptide, oligonucleotide, or an organic molecule is delivered in a manner consistent with the conventional methods associated with the treatmnent of the particular disease such for example orally, intravenously, intramuscularly, topically, subcutaneously or by aerosol inhalant in order to prevent the inflammatory reactions associated with such diseases.

What is claimed is:

1. A method of identifying compounds for treatment of mast cell mediated inflammatory disorders in mammals comprising
   (a) applying said compound to mast cells,
   (b) measuring expression/function of an anti-apoptotic A-1/bfl-1 gene or gene product,
   (c) identifying whether said compound decreases said expression/function of said gene or gene product involved in mast cell mediated inflammatory disorders in comparison to mast cells to which said compound is not applied, and
   (d) identifying an expression/function-decreasing compound as a candidate compound for treatment of mast cell mediated inflammatory disorders.

2. A method of selecting for candidate drugs for treatment of mast cell mediated inflammatory disorders in mammals comprising (a) using the anti-apoptotic A-1/bfl-1 gene or gene product as a molecular target,
(b) selecting a compound which binds to the A-1/bfl-1 gene or gene product involved in mast cell mediated inflammatory disorders, and
(c) designating compounds selected in step (b) as candidate drugs for treatment of mast cell mediated inflammatory disorders.

* * * * *

UNITED STATES PATENT AND TRADEMARK OFFICE
CERTIFICATE OF CORRECTION

PATENT NO.      : 6,465,187 B1
DATED           : October 15, 2002
INVENTOR(S)     : Gunnar Nilsson and Zou Xiang It is certified that error appears in the above-identified patent and that said Letters Patent is hereby corrected as shown below:

Drawings,
Drawing sheet 9 of 11, Fig, 9B should appear as follows:

FIG. 9B

Signed and Sealed this

Eleventh Day of February, 2003

JAMES E. ROGAN
*Director of the United States Patent and Trademark Office*